United States Patent
Rokugawa et al.

[11] Patent Number: 5,554,811
[45] Date of Patent: Sep. 10, 1996

[54] AUTOMATIC CHEMICAL ANALYZERS WITH SAMPLING SYSTEMS

[75] Inventors: Kyuji Rokugawa, Nishinasuno-Machi; Kouji Matsumoto, Otawara; Morito Inoue, Nishinasuno-Machi, all of Japan

[73] Assignee: Kabushiki Kaisha Toshiba, Kawasaki, Japan

[21] Appl. No.: 380,998

[22] Filed: Jan. 31, 1995

Related U.S. Application Data

[62] Division of Ser. No. 70,995, Jun. 4, 1993, Pat. No. 5,415,051.

[30] Foreign Application Priority Data

Mar. 2, 1993 [JP] Japan .................................. 5-041314

[51] Int. Cl.$^6$ .......................... G01N 21/75; G01N 35/10
[52] U.S. Cl. .................... 73/864.34; 73/863.32; 422/82.09
[58] Field of Search ............ 422/82.09; 73/864.34, 73/864.11, 864.21, 863.01, 864.35, 863.02, 863.03, 864.62, 864.81–864.87, 863.32

[56] References Cited

U.S. PATENT DOCUMENTS

| | | | |
|---|---|---|---|
| 3,649,204 | 3/1972 | Farr | 73/864.85 X |
| 3,985,028 | 10/1976 | Yoshida | 73/863.03 X |
| 4,158,545 | 6/1979 | Yamashita et al. | 422/67 X |
| 4,313,735 | 2/1982 | Yamashita et al. | 422/64 X |
| 4,318,615 | 3/1982 | Sagusa et al. | 356/320 |
| 4,451,433 | 5/1984 | Yamashita et al. | 422/64 X |
| 4,696,183 | 9/1987 | Mitsumaki et al. | 73/863.01 X |
| 4,794,806 | 1/1989 | Nicoli et al. | 73/863.01 |
| 4,893,515 | 1/1990 | Uchida | 73/864.34 |
| 4,939,095 | 7/1990 | Yokotani | 422/64 X |
| 4,944,922 | 7/1990 | Hayashi | 73/863.02 X |

FOREIGN PATENT DOCUMENTS

| | | | |
|---|---|---|---|
| 108639 | 7/1982 | Japan . | |
| 251771 | 11/1986 | Japan | 422/82.09 |
| 131066 | 6/1988 | Japan | 422/82.09 |
| 78957 | 3/1990 | Japan | 422/82.09 |
| 59461 | 3/1991 | Japan | 422/82.09 |
| 272467 | 12/1991 | Japan | 422/82.09 |

*Primary Examiner*—Thomas P. Noland
*Attorney, Agent, or Firm*—Oblon, Spivak, McClelland, Maier, & Neustadt, P.C.

[57] ABSTRACT

A sampling system, favorably applicable to an automatic chemical analyzer, is provided for sampling by sucking and discharging liquid, such as specimens and reagents. The sampling system comprises a pump having a container in which an inner space of a certain volume is formed and an actuator arranged in the inner space to fore a pumping chamber therein. The actuator comprises a base plate having both sides thereon and a piezoelectric element attached to the base plate. Further provided are a tube having one end connected to the pumping cheer, a nozzle connected to another end of the tube, and an element for controlling a driving voltage applied to the piezoelectric element. For instance, the piezoelectric element is composed of two piezoelectric plates attached each to both the sides of the base plate. A piezoelectric sensor is attached to the base plate for detecting distortion of the actuator, a liquid level of specimens and reagents, and error operations such as air suction and jamming. The piezoelectric sensor is attached to a cutout portion, partly cut out in either one of two piezoelectric plates. In case of being applied to the automatic chemical analyzer, an output signal from the piezoelectric sensor is used for correction of absorbance data.

24 Claims, 10 Drawing Sheets

AUTOMATIC CHEMICAL ANALYZERS WITH SAMPLING SYSTEMS

This is a Division of U.S. patent application Ser. No. 08/070,995 filed on Jun. 4, 1993, and now U.S. Pat. No. 5,415,051.

BACKGROUND OF THE INVENTION

The present invention relates to an automatic chemical analyzer for specimen tests such as chemical analysis and immunoassay in a field of clinical tests, and in particular, to sampling systems for specimens and reagents in the automatic chemical analyzer. The terms "sampling" and "sample" used herein are employed to mean that liquids (i.e., specimens and/or reagents) are sucked at one position, delivered to another position, and then discharged.

At present, automatic chemical analyzers have been utilised preferably for specimen tests, such as chemical analysis and immunoassay. In general, to relieve a patient of his or her burden against extracting his or her specimen and to reduce reagents to their minimums, the analyzer adopts a microquantity sampling technique of high accuracy by which a minimum specimen sampling quantity of 2 μl per test and a coefficient of variation: CV of 1% or less have been realized. The coefficient of variation: CV is represented by an equation: CV %=(standard deviations of measuring values)/(mean values of measuring values)×100.

Such high accuracy sampling requires each element part (component) of the analyzer to be highly accurate in operation, which has led to continuing technical development; for example, increases in operating accuracy for syringes and driving systems of sampling pumps, prevention of the pressure loss through the pressure transmitting system ranging from a syringe to a pipetting probe, and quick response of valves.

However, raising the operation accuracy of each component of an automatic chemical analyzer up to almost their limits using such techniques has been attended with a number of technical difficulties, which results primarily in a large increase in manufacturing cost.

Furthermore, there are other drawbacks in conventional-type analyzers. One of them is concerned with their size. Sampling exactly-specified quantities(volumes) of specimens and reagents from a pipetting probe into a reaction cup requires a large number of sensors to be installed in the analyzer, which leads to an unfavorable increase in the entire size of the analyzer.

Another drawback is a problem of contamination of pipetting probes. It is necessary to prevent the tip of a pipetting probe from being contaminated by specimens or reagents for reducing the volume of reagents. To avoid excessive contamination, a device has been used in which only a minimum length of the tip of the pipetting probe is dipped into specimens or reagents. This device necessitates sensors for detecting liquid levels in specimen and reagent cups. Such sensors utilize, for instance, changes in electrical conductance or capacitance.

However, the sensor utilizes changes in electrical conductance, even though it shows favorable sensitivity to conductive liquid solution only, is required to have two electrodes. Therefore, there exists a drawback; liquid solution tends to stick to the ends of the electrodes to remain therebetween. On one hand, the sensor based on capacitance changes, in which one electrode is used, can use a pipetting probe able to work also as the electrode. But, in this sensing system, because of the non-conductiveness of cups from which specimens or reagents are sampled, the sensitivity in detection is decreased and this system can not be easily used for microquantity sampling.

A further drawback common to both the conductivity-depended and capacitance-depended sensors is as follows; when a pipetting probe is also used as an elctrode, the pipetting probe itself should be made of conductive metal. Thus such sensors not be used, when plastic-made disposable pipetting probes (chips) are used.

Furthermore, there is a problem which needs to be solved in conventional analyzers. That is a problem concerning a detection of air suction while being sampled and detecton of jamming at a pipetting probe with impurities in liquid solution such as fibrin in a serum specimen. For detecting Jamming, a semiconductor pressure sensor is disposed in the pipetting probe to detect inner pressure changes therein. However, the semiconductor pressure sensor is a complex construction device and is difficult to deaerate air. In addition, the semiconductor pressure sensor tends to fail, and has a limit in sensitivity; it can not be applied to sampling handling a microquantity of 20 μl or less.

SUMMARY OF THE INVENTION

Accordingly, it is an object of the present invention to provide an automatic chemical analyzer with sampling systems which is low manufacturing cost, compact size and accurate in measured values.

It is a further object of the present invention to provide an automatic chemical analyzer which is able to precisely sample specimens and reagents even if their sampling quantities per one time are quite small, thereby increasing measurement accuracy.

It is a still further object of the present invention to provide an automatic chemical analyzer in which absorbance data collected are adequately corrected, if required, according to specified sampling quantities.

It is a still further object of the present invention to provide an automatic chemical analyzer having pipetting probes to be able to detect liquid levels and/or errors, such as air suction and Jamming with impurities.

These and other objects can be achieved according to the present invention, in one aspect by providing, a sampling system for sucking and discharging liquid, comprising: a pump having a container in which an inner space of a certain volume is formed and an actuator arranged in the inner space to form a pumping chamber therein, the actuator comprising a base plate having both sides thereon and a piezoelectric element attached to the base plate; a tube having one end connected to the pumping chamber; a nozzle connected to another end of the tube; and an element for controlling a driving voltage applied to the piezoelectric element.

It is preferred that the sampling system is applied to an automatic chemical analyzer.

In another aspect by providing, an automatic chemical analyzer having a sampling system in which a liquid including a specimen and a reagent is sampled by sucking the liquid at one position and discharging the sucked liquid at another position, resultant chemical raction between the specimen and the reagent being detected as an absorbance data collected for chemical analysis, the sampling system comprising: a pump having a pumping chamber for sucking and discharging the liquid; a tube having one end connected to the pumping chamber; a nozzle connected to another end of the tube; an element for driving the pump to sample a certain quantity of the liquid by sucking and discharging the liquid; a sensor for sensing an operating quantity of the pump and generating a signal corresponding to the operating quantity; an element for determining the sampling quantity sampled by the pump in response to the signal from the sensor; and an element for correcting the collected absorbance data in accordance with the determined sampling quantity.

Preferably, the pump has a container in which an inner space of a certain volume is formed and an actuator arranged in the inner space to form the pumping chamber therein, the actuator comprising a base plate having both sides thereon and a piezoelectric element attached to the base plate.

It is preferred that the piezoelectric element is composed of two piezoelectric plates attached each to both the sides of the base plate. One piezoelectric plate attached to either one of both the sides of the base plate is possible.

In a preferred embodiment, the controlling element and driving element include a circuit for controlling the driving voltage in a manner that, for sucking the liquid, the piezoelectric element displaces from an original state to a distortion state to increase the volume of the pumping chamber and, for discharging the liquid, the piezoelectric element returns from the distortion state toward the original state. The controlling element includes a piezoelectric sensor for sensing distortion of the actuator. The piezoelectric sensor is attached to the base plate and generates a signal corresponding to the distortion.

It is preferred that either one of two piezoelectric plates is partly cut out to form a cutout portion and the piezoelectric sensor is attached to the cutout portion. Also included is an element for determining a sampling quantity through the nozzle in response to the signal from the piezoelectric sensor.

It is preferred that an element for detecting a level of the liquid and an element for detecting an error in sampling, in response to the signal from the piezoelectric sensor, are provided. The error is air suction from the nozzle and/or jamming at the nozzle with impurities contained in the liquid.

In another preferred embodiment the analyzer further comprises an element for calculating a desired measuring value using the absorbance data corrected by the correcting element.

BRIEF DESCRIPTION OF THE DRAWINGS

The accompanying drawings which are incorporated in and constitute a part of this specification, illustrate embodiments of the present invention and, together with the description, serve to explain the principles of the present invention. In the drawings.

DESCRIPTION OF THE PREFERRED EMBODIMENTS

A first embodiment of the present invention will now be described with reference to FIGS. 1 to 9.

Figure 1:
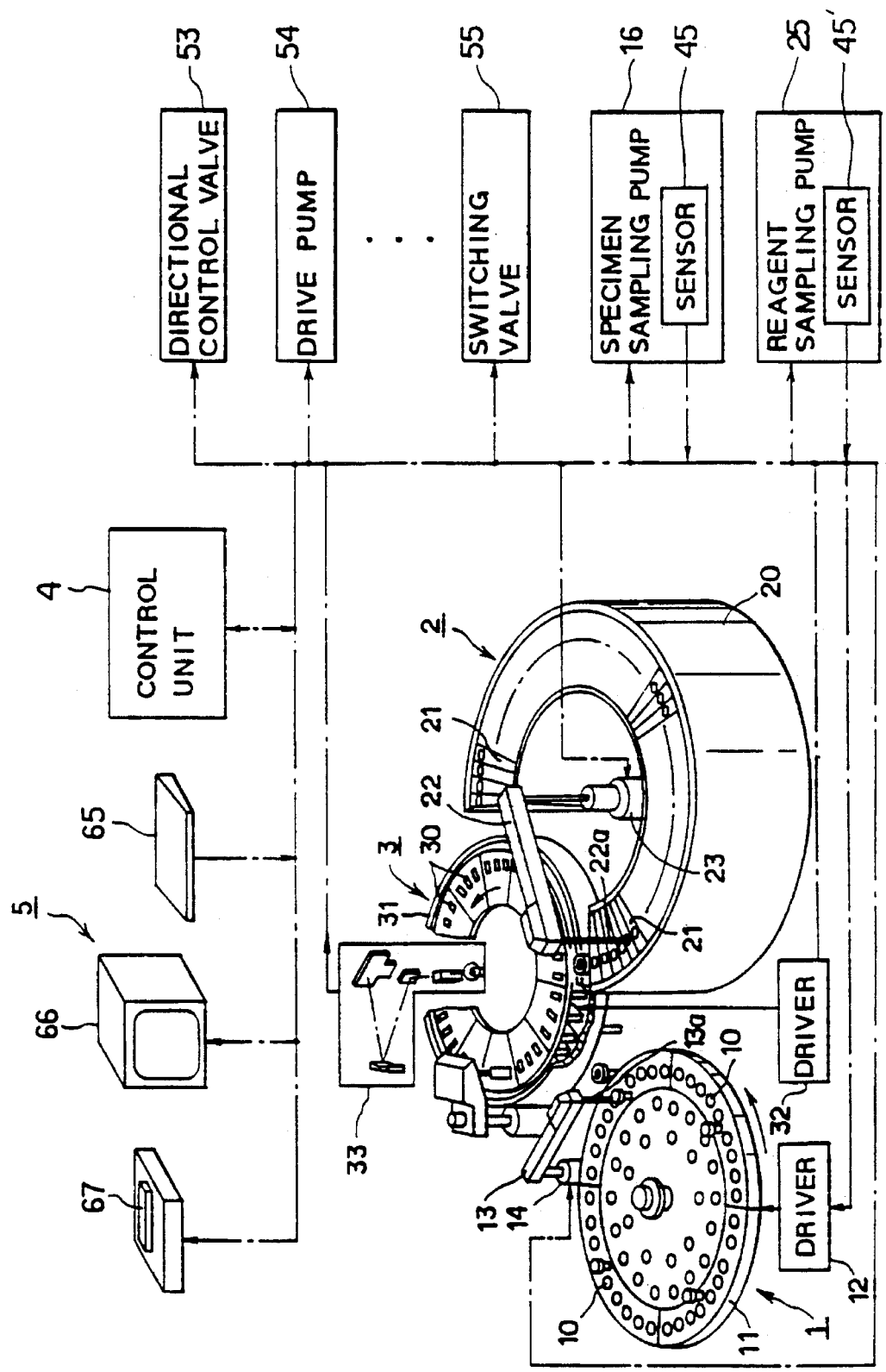
FIG. 1 is a block diagram showing an automatic chemical analyzer with sampling systems according to a first embodiment of the present invention.
Figure 2:
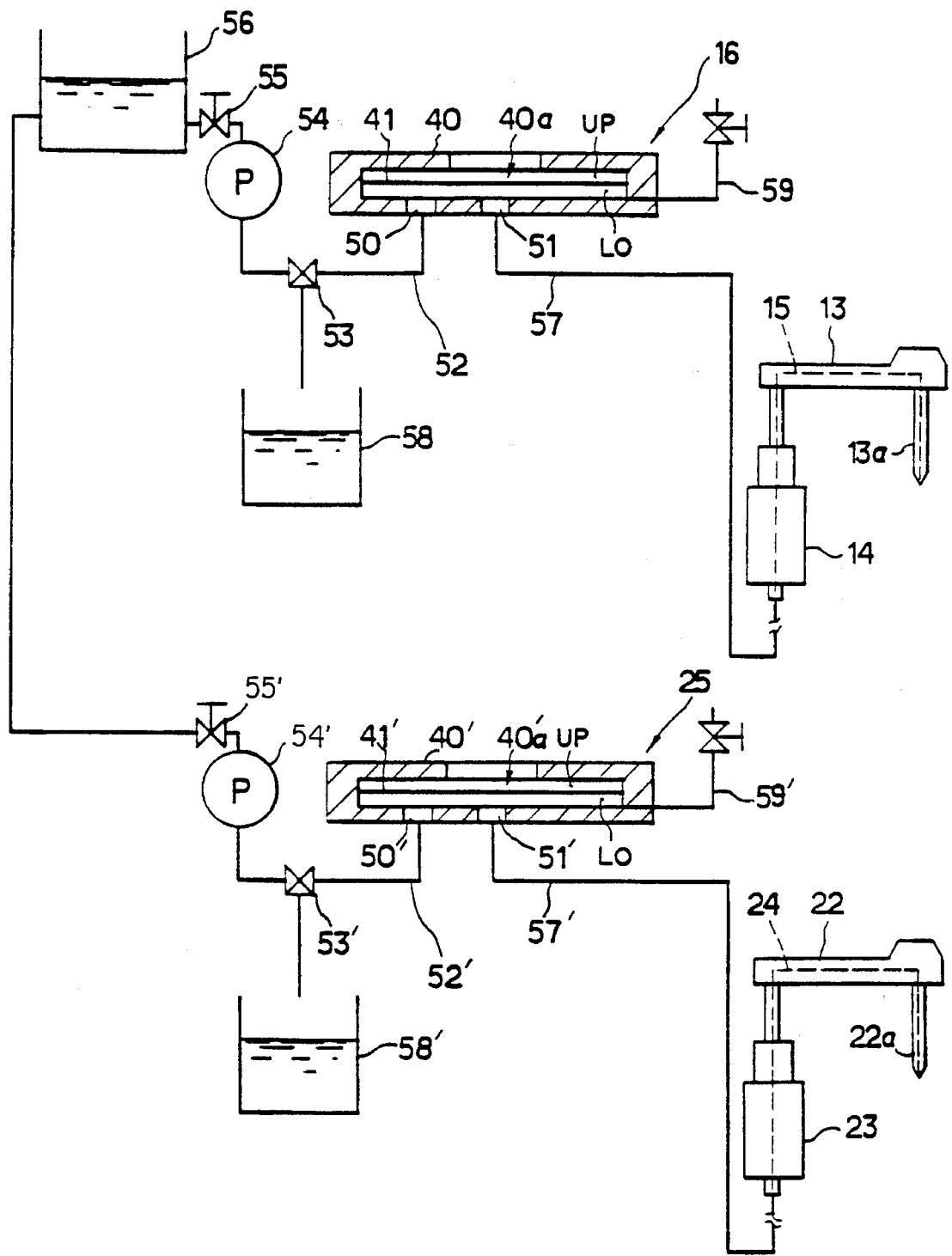
FIG. 2 is a diagram representing an essential part of fluid passages of the analyzer in the first embodiment.

In FIGS. 1 and 2, there is shown an automatic chemical analyzer according to the first embodiment, which is used for biochemical analysis or immunoassay. FIGS. 1 and 2 represent essential parts of an electric connection and a fluid connection among components of the automatic chemical analyzer, respectively.

As shown in FIG. 1, the automatic chemical analyzer comprises a first unit 1 concerning specimens, a second unit 2 concerning reagents, a third unit 3 concerning reaction, a control unit 4, and an input/output unit 5.

The first unit 1 concerning specimens has a plurality of specimen cups 10 ... 10 with which a specimen is filled, a specimen disk 11 formed for holding the specimen cups 10 ... 10 detachably on the disk 11, a specimen disk driver 12 for driving the specimen disk 11 in response to a driving signal supplied from the control unit 4. The specimen cup 10 ... 10 are aligned in a circle form when viewed from the upper side of the disk 11.

Further, the first unit 1 comprises a single specimen sampling arm 13 for sampling the specimen from the speimen cups 10 ... 10 to a plurality of reaction cups later-described, and an arm driver 14 for driving the specimen sampling arm 13 in response to a driving signal from the control unit 4. The specimen sampling arm 13 is formed into an inversed L-letter shape and is movable vertically and rotatable horizontally with respect to its base axis portion.

From an end of the arm 13, a specimen pipetting probe 13a is fixedly suspended, the pipetting probe 13a being formed into a hollow needle and working as a nozzle. The probe 13a is connected via a fluid passage 15 passing through the arm 13 to a specimen sampling pump 16 (refer to FIG. 2).

The specimen disk 11 is rotatable under control of the control unit 4, thus each of the specimen cups 10 ... 10 can be placed at a predetermined specimen suction position by controlling a rotation angle of the specimen disk 11.

In the second unit 2 concerning reagents, a reagent storage 20 is provided adjacent to the specimen disk 11 and formed into a horse-shoe shape when viewed from its upper side. Also provided are a plurality of reagent bottles 21 ... 21 detachably inserted into the reagent storage 20, a reagent sampling arm 22 for sampling the reagent from the reagent bottles 21 ... 21 to the plurality of reaction cups later-described, and an arm driver 23 for driving the reagent sampling arm 22 in response to a driving signal from the control unit 4. The reagent sampling arm 22 is also formed into an inversed L-letter shape, and is movable vertically and rotatable horizontally with respect to its base axis portion.

From an end of the arm 22, a reagent pipetting probe 22a is fixedly suspended, the pipetting probe 22a being formed into a hollow needle and working as a nozzle. The probe 22a is connected via a fluid passage 24 passing through the arm 22 to a reagent sampling pump 25 (refer to FIG. 2).

In the third unit 3 related to reaction, there are provided a plurality of reaction cells 30 ... 30 which are transparent, a reaction disk 31 for detachably holding the reaction cells 30 ... 30 in a circle form when viewed from its upper side, a reaction disk driver 32 for rotating the reaction disk 31 in a counterclockwise direction in response to a driving signal from the control unit 4, and an optical measuring device 33 for optically detecting absorbance data of the reaction cells 30 ... 30 as a representative of concentration of a substance contained therein.

The optical measuring device 33 comprises a light source having multiple-wavelengths, mirrors, a concave diffraction grating, and a photodiode array. A light axis traveling from the light souce through the mirrors will be crossed by the reaction cells 30 ... 30, thus light quantities corresponding to each absorbance data of the cells 30 ... 30 will be changed into an electrical detection signal to be sent out to the conrol unit 4.

Figure 3A:
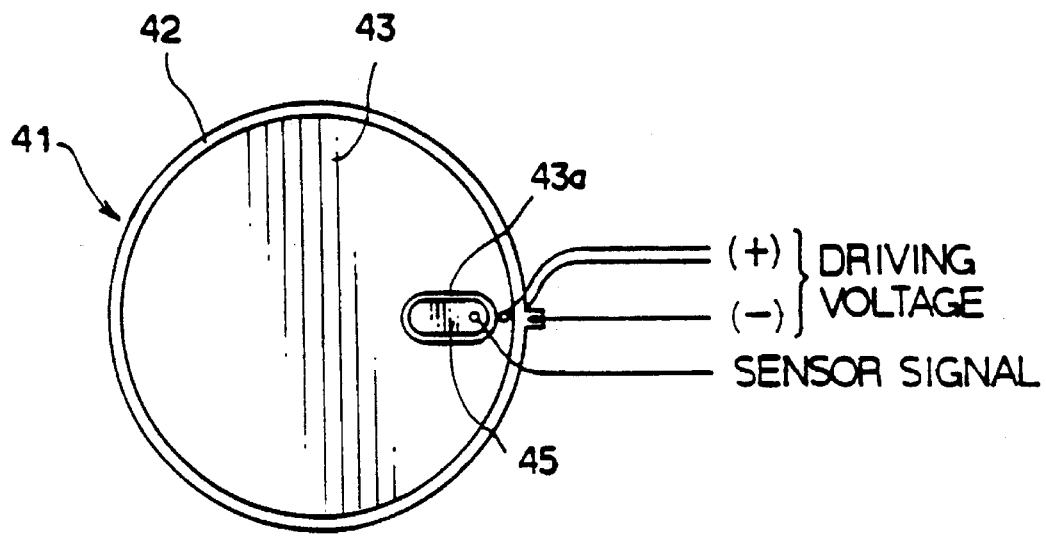
FIGS. 3A and 3B are views for showing an actuator having piezoelectric elements.
Figure 3B:
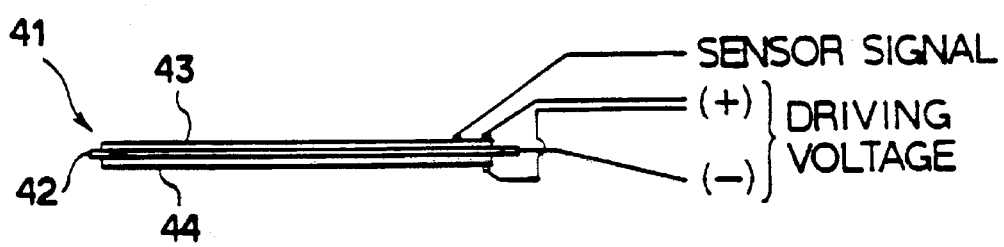

Each of the above specimen and reagent sampling pumps 16 and 25, in this embodiment, employs a piezoelectric pump as a diaphragm type pump, as shown in FIGS. 2, 3A and 3B. Each pump 16(25) has a disk like container 40(40') having an inner cylindrical space (40a(40a') and an actuator 41(41') fixedly displaced in the inner space 40a(40 a').

In detail, the actuator 41 comprises a thin, circular metal plate 42 as a base plate as shown in FIG. 3A and two thin, circular piezoelectric sheets 43 and 44 attached to both the sides of the metal plate 42. Two pairs of driving voltages will be supplied each to the piezoelectric sheets 43 and 44 from the control unit 4. This provides bimorph type piezoelectric elements, because two piezoelectric sheets 43 and 44 will work as piezoelectric transducers at both sides of the actuator 41.

Figure 3C:
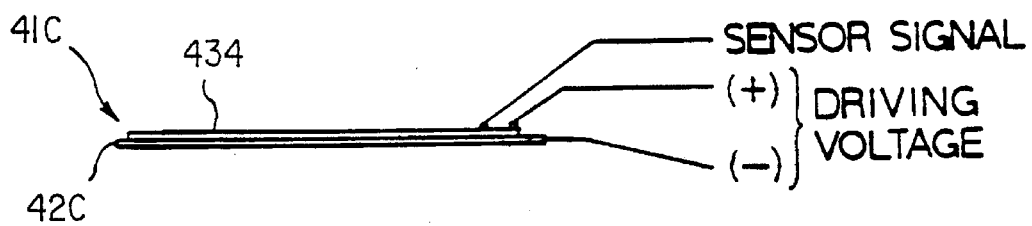
FIG. 3C shows an alternative embodiment of the actuator.

FIG. 3C shows an alternative embodiment of the actuator showing an actuator 41c comprising a metal plate 42c with a piezoelectric sheet 434 on one side thereof.

In the inner space 40a, the metal plate 42 is in parallel with its wall and bottom so as to divide it into two pump chambers: an upper chamber UP and a lower chamber LO. At the side of the upper chamber UP in this embodiment, as illustrated in FIG. 3A, there is formed a cutout portion 43a in the piezoelectric sheet 43. In this cutout portion 43a, a piezoelectric sensor 45, separetely from the sheet 43, is fixedly attached to detect mechanical distortion of the actuator 41 and exchange it into an electrical detection signal in accordance with the degree of the distortion. The detection signal outputted from the sensor 45 is supplied to the control unit 4. Each sampling pump 16(25) has two ports 50(50') and 51(51') at its lower pump chamber LO as seen in FIG. 2. One port 50(50') is connected by a tube 52(52') through a 3-way directional control valve 53(53'), an electromagnetic drive pump 54(54') for washing, and an electromagnetic switching valve 55(55') to a water storage tank 56 containing washing water such as pure water. Further the rest port of the 3-way directional control valve 53(53') is connected to a drain tank 58(58') for storing; drain water from the lower pump chamber LO after its washing. The other port 51(51') is connected via a sampling tube 57(57') to the aforementioned pipetting probe 13a(22a). The sampling tube 57(57') will work as a system for transmitting pressure therebetween. There is a deaeration passage 59(59'); coupled with the lower pump chamber LO.

Figure 4:
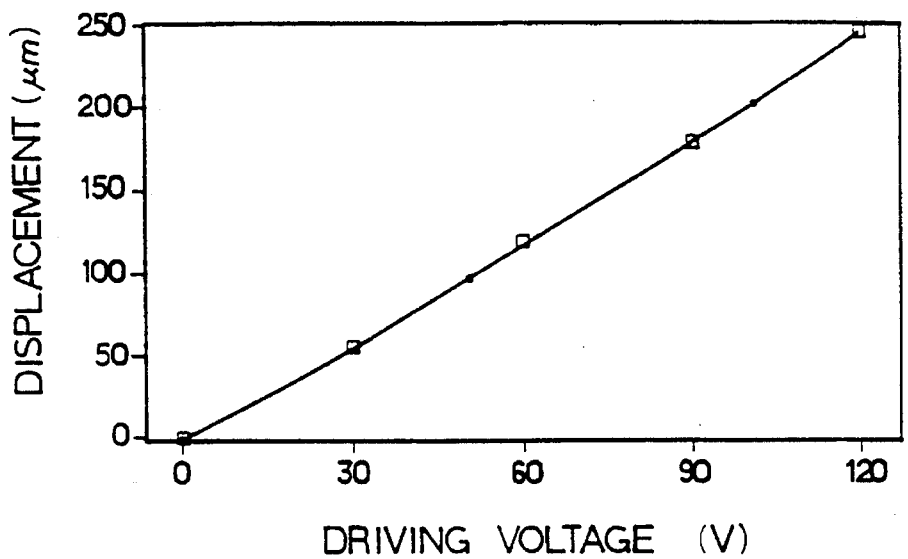
FIG. 4 is a correlation between driving voltages to the actuator and its displacements.

In FIG. 2, the fluid passages for pumping will be filled with washing water (such as pure water) deaerated. Then driving voltages will be applied to the actuators 41 and 41' and then will be stopped. This will cause the actuators 41 and 41' to displace so as to generate pressure changes, so that the pipetting probes 13a and 22a can suck a given volume of specimen and reagent from its their tips and can discharge them, respectively, the volume being specified by the driving voltage to the actuator 41. FIG. 4 shows the relationship between a driving voltage suppliying to the actuator 41 and its displacement quantities.

Further, data of sampling properties for the above sampling pump 16 (25) was obtained as shown in Table 1. The sampling properties represent, with respect to each of changed driving voltages 0 to 120 v, trial numbers of test, displacement quantities of a diaphragm (i.e., the actuator 41), and discharge quantities (i.e., the volumes of specimen or reagent) at one sampling time. As seen from Table 1, with an increase from 0 to 120 v in driving voltages, the discharge quantity is also increased, even though there is dispersion to some extent.

TABLE 1

| Driving Voltage (V) | No. of Test | Displacement Qt. (μm) | Discharge Qt. (μl) |
|---|---|---|---|
| 0 | 1 | 0.0000 | 0.0 |
| | 2 | 0.0000 | 0.0 |
| | 3 | 0.0000 | 0.0 |
| | 4 | 0.0000 | 0.0 |
| | 5 | 0.0000 | 0.0 |
| 10 | 1 | 11.7180 | 7.3 |
| | 2 | 17.1880 | 9.9 |
| | 3 | 14.0630 | 8.7 |
| | 4 | 14.8440 | 8.7 |
| | 5 | 9.3750 | 5.9 |
| 30 | 1 | 53.1250 | 31.5 |
| | 2 | 52.3440 | 31.5 |
| | 3 | 52.3430 | 31.3 |
| | 4 | 47.6570 | 28.8 |
| | 5 | 53.1250 | 31.7 |
| 60 | 1 | 115.6250 | 69.4 |
| | 2 | 114.8440 | 69.1 |
| | 3 | 114.8440 | 69.0 |
| | 4 | 108.5940 | 65.6 |
| | 5 | 111.7190 | 68.0 |
| 90 | 1 | 180.0000 | 108.7 |
| | 2 | 178.0000 | 106.2 |
| | 3 | 180.0000 | 109.6 |
| | 4 | 177.0000 | 106.0 |
| | 5 | 171.0000 | 103.0 |
| 120 | 1 | 246.0000 | 148.2 |
| | 2 | 245.0000 | 146.8 |
| | 3 | 245.0000 | 147.4 |
| | 4 | 233.0000 | 136.8 |
| | 5 | 235.0000 | 140.2 |

Figure 5:
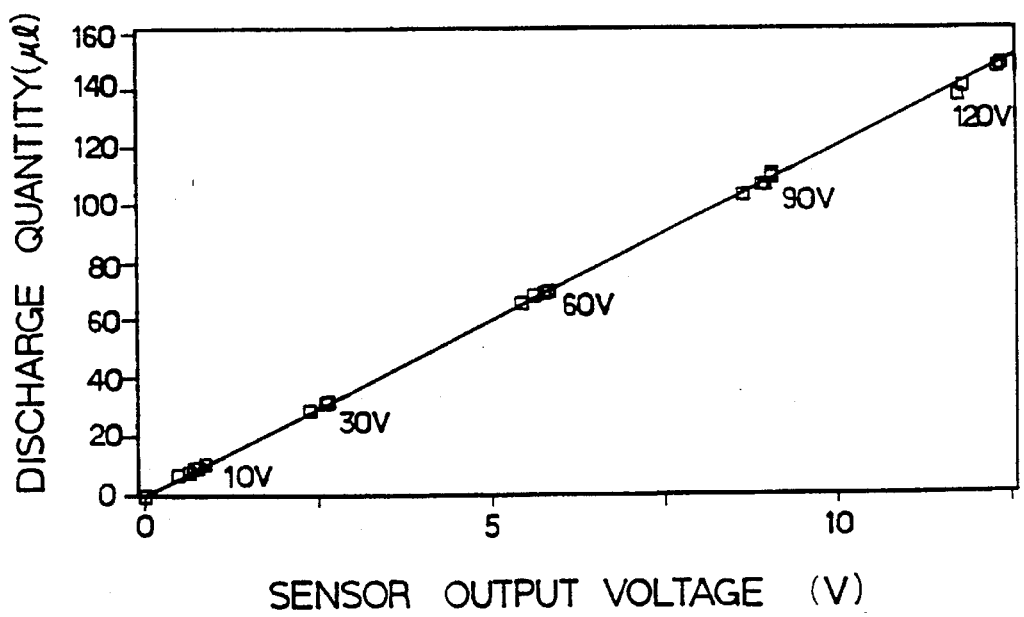
FIG. 5 is a correlation between sensor output voltages and discharge quantities.

In addition, FIG. 5 shows a correlation between sensor output voltages (representing the displacement quantities) and the discharge quantities plotted using the data shown in Table 1; it clearly represents a linear correlation.

Based on FIG. 5, it has been found that measuring volages detected by the piezoelectric sensor 45 of the actuator 41 at every sampling can teach a volume of sampling (i.e., volumes of specimen and reagent) per one time.

On one hand, using the above sampling pump 16 (25), detectability of a liquid level at the tip of the pipetting probe 13a (22a) has been tested. When the tip of the pipetting probe 13a(22a) comes into contact with a liquid level, the diaphragm of the sampling pump 16(25), in other words, the actuator 41, is slightly displaced toward its negative side. This displacement is caused by a negative pressure occurring inside the pippeting probe 13a(22a) when the tip of the probe 13a (22a) reaches the liquid surface.

Figure 6:
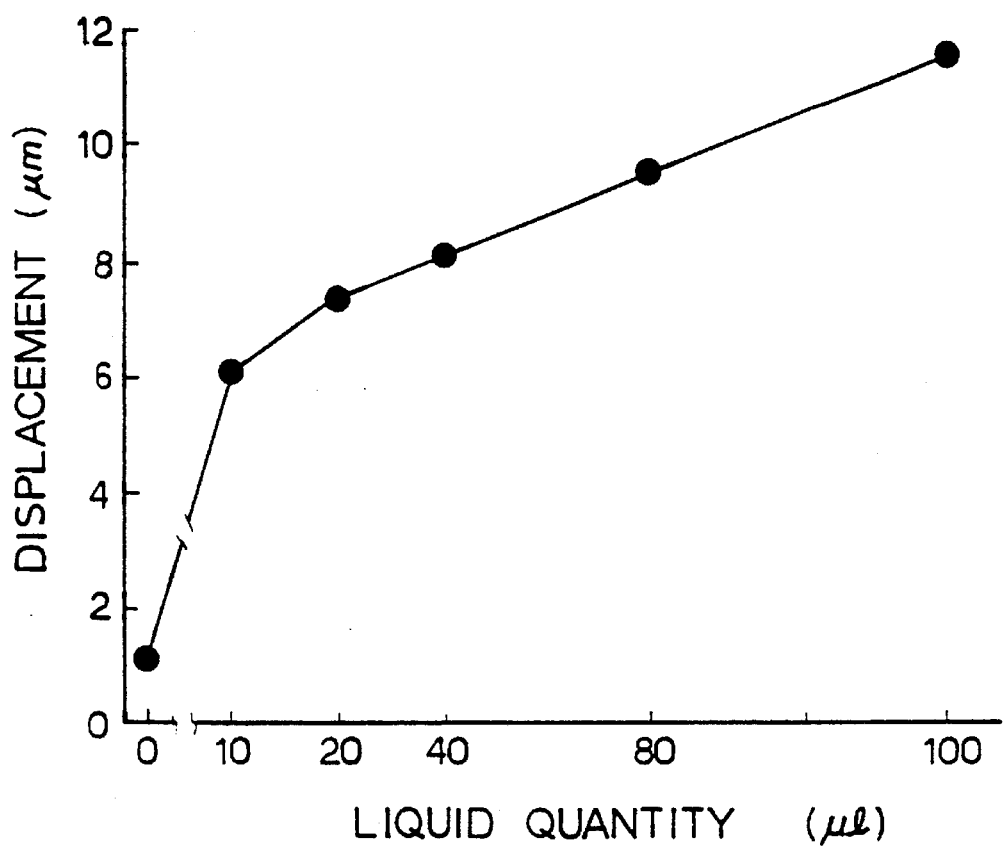
FIG. 6 is a correlation between liquid quantities contained in a cup and displacements of the actuator.

For the above contact displacement, FIG. 6 has been obtained, which shows a correlation between displacement quantities μm of the actuator 41 and the volumes of liquid μl contained in a cup (such as the specimen cup and the reagent bottle). In FIG. 6, one can see that, whereas the displacement quantity is 1 μm or less where there is no liquid in the cup, it is 6 μm or more where there is amounts of liquid of 10 μl or more in the cup. On top of it, it is found that the displacement quantity increases with an increase in the volume of liquid in the cup. .Therefore, the combination of the sampling pump 16 (25) and pipetting probe 16a (22a) may be used as a sensor for detecting liquid levels with extremely high sensitivity.

Figure 7A:
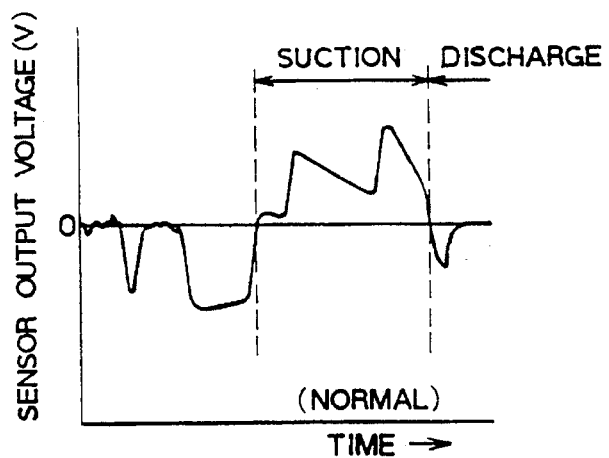
FIGS. 7A to 7C represent wave forms of the sensor output voltages in normal state, air suction state, and jamming state, respectively.
Figure 7B:
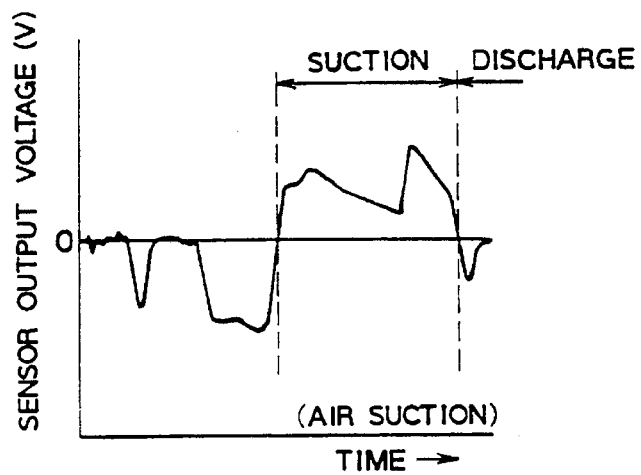
Figure 7C:
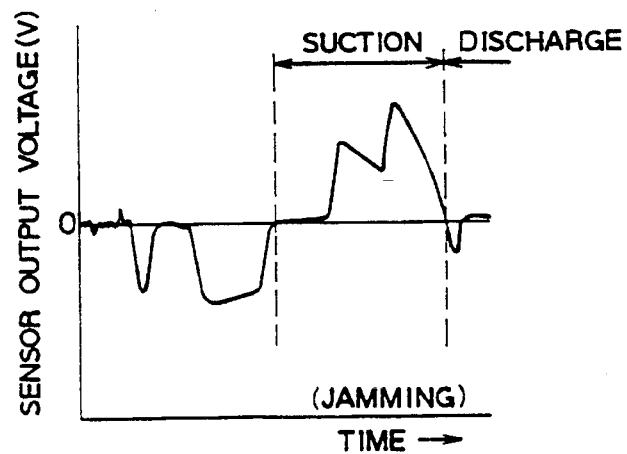

Furthermore, when the above-mentioned pipetting probe 13a (22a) is made to suck air, water and serum, respectively, from its tip, and is jammed at its tip, wave patterns of the sensor output voltage vs. elapsed time have been found as shown in FIGS. 7A to 7C. It is clear that there are remarkable differences in their wave patterns, especially in their first transitions of suction among a normal state (shown in FIG. 7A), an air suction state (shown in FIG. 7B), and a jamming state (shown in FIG. 7C). Compared with the pattern of FIG. 7A, the first transition of suction in FIG. 7B is sharper and immediately rises up and in contrast that in FIG. 7C is gradual and reluctant to rise up. Therefore, examining the differences in the wave patterns enables the analyzer to distinguish their error states.

Further, it has been found that response of the actuator 41 is exellent in samplings of not only large volumes of liquid but micro-volumes of 10 μl or less, and sensitively detected.

Figure 8:
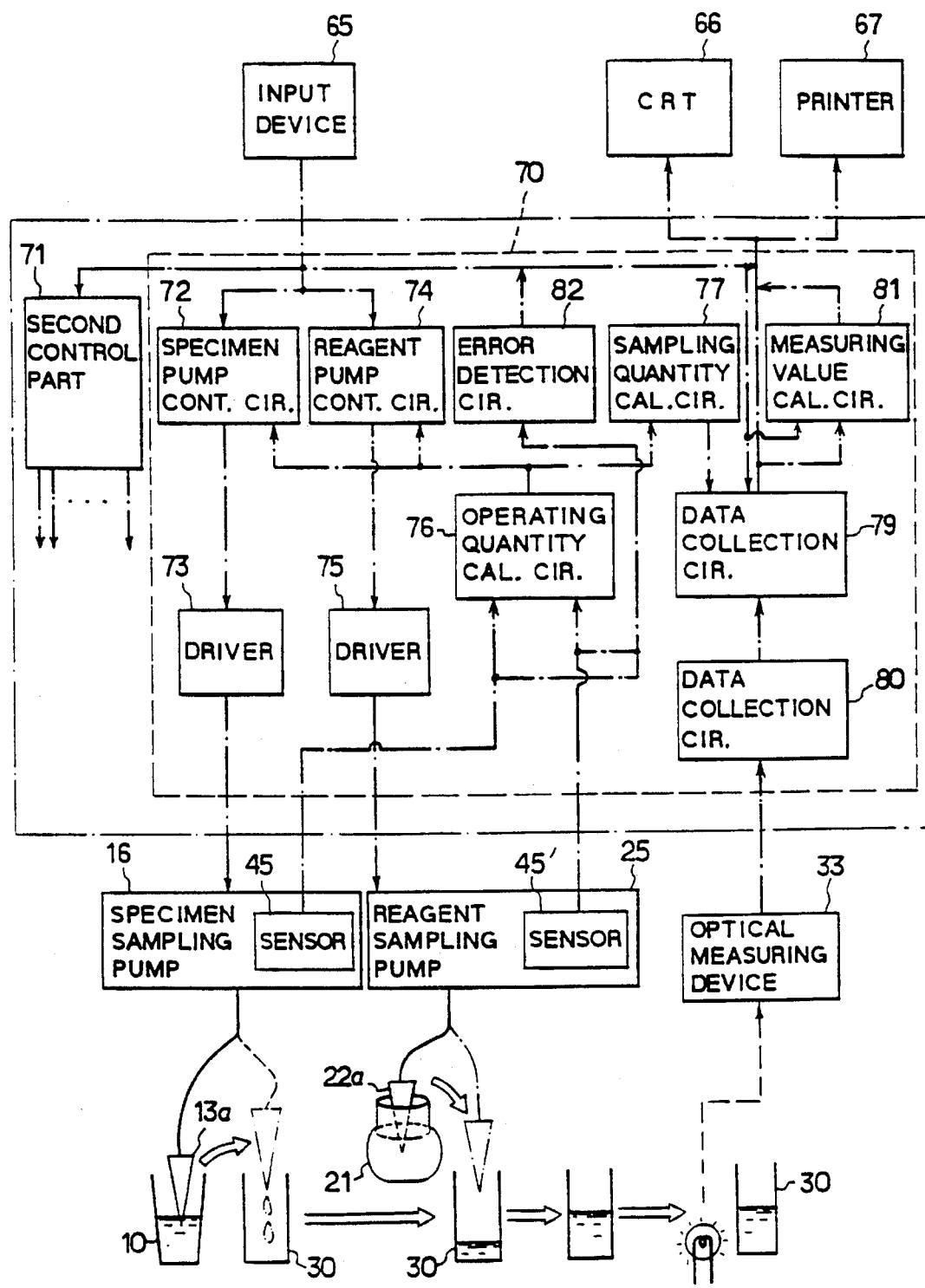
FIG. 8 is a block diagram representing an essential part of electric circuits of the analyzer in the first embodiment.

The aforementioned input/output unit 5, as shown in FIGS. 1 and 8, has an input device 65, a CRT (cathode ray tube) 66, and a printer 67. The input device 65 is used for inputting information including desired test items in biochemical analysis or immunoassay. The CRT 66 and printer 67 are provided for displaying necessary information including raw absorbances and finally calculated measuring values.

Further, the aforementioned control unit 4 will be described according to FIG. 8.

In the control unit 4, there are provided a first control part 70 for controlling the sampling pumps 16 and 25 and processing collected data and a second control part 71 for controlling the other components of the analyzer.

The first control part 70 comprises, as shown in FIG. 8, a specimen pump control circuit 72, a specimen pump driver 73, a reagent pump control circuit 75, and a reagent pump driver 76. In accordance with test items supplied form the input device 65, both of the control circuits 72 and 74 will send control signals corresponding to regulated driving voltages to both the drivers 73 and 75. The drivers 73 and 75 will each provide the specimen and reagent sampling pumps 16 and 25 pulsed driving voltages in proportion to the value of the driving signals.

In the first control part 70, there is further provided an operating quantity calculation circuit 76 for receiving detected voltage signals outputted from both the piezoelectric sensors 45 and 45', which are embedded in each of the actuators 41 and 41' of the specimen and reagent sampling pumps 16 and 25 as have been described above. The operating quantity calculation circuit 76 is to determine operating quantities (liquid volumes) using the detected sensor voltages, individually for both the sampling pumps, and supply them to both of the control circuits 72 and 74.

In respose to the sensor voltages thus-received, both of the control circuits 72 and 74 will regulate the control signals by feedback control technique. In consequence, the operation of sampling itself should be regulated.

The operating quantities determined by the calculating circuit 76 is to be sent to a sampling quantitiy calculation circuit 77, which exists in the first control part 70. The sampling quantitiy calculation circuit 77 is designed so as to determine sampling quantities of a specimen and a reagent on the basis of the operating quantities calculated, the sampling quantities thus-determined being sent to a data correction circuit 79.

Further, in the first control part 70, there is provided a data collecting circuit 80 for collecting the data of absorbances time-dependently detected by the optical measuring device 33. The data of absorbances will then be sent out to the data correction circuit 79.

Figure 9:
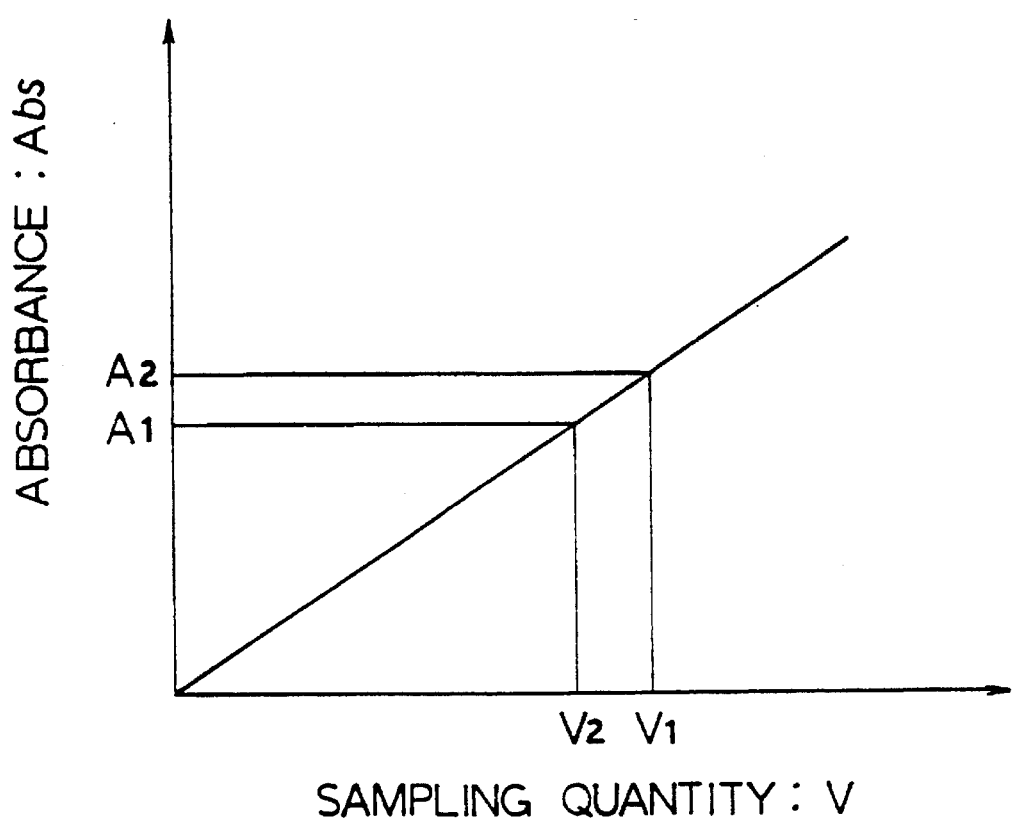
FIG. 9 is a correlation between sampling quantities and absorbances.

The data correction circuit 79 has a mechanism which corrects data automatically in response to the actually-measured absorbance data, if necessary; for example, as shown in FIG. 9, a predetermined calibration curve showing a correlation between absorbances: Abs and sampling quantities: V of specimen or reagent is used. In FIG. 9, whereas the sampling quantity V=V1 is specified by the input device 65, the actually detected sampling quantity might be V=V2. In such a case, the absorbance Abs will be corrected from Abs=A1 to Abs=A2, the absorbance thus-corrected can be displayed on the CRT 66 and printer 67. The data of the calibration curve in FIG. 9 can be pre-stored in a memory of the correction circuit 79.

The corrected data of absorbance are sent to a measuring value calculation circuit 81 which constitute a part of the first control part 70. In the measuring value calculation circuit 81, concentration of substances to be measured, contained in specimens, will be calculated according to a calibration curve or factors. The measuring value thus-obtained will be sent to the CRT 66 and printer 67 for display.

Furthermore, in the first control part 70, there is an error detection circuit 82 receiving the sensor outputs from the above-mentioned piezoelectric sensors 45 and 45'. The error detection circuit 82 is composed so that the wave patterns of the sensor voltages are analyzed to judge the degree of deviation from the normal pattern shown in FIG. 7A. Thus, the state of air suction or jamming will be known and displayed.

Now the entire operation of the analyzer will be described.

When a desired test item is specified by the input device 65, the second contol part 71 works, as a resut, the reaction disk 31 should be rotated in a counterclockwise direction and each of the reaction cells 30 . . . 30 are carried in turn to a given specimen sampling position and then a given reagent sampling position.

In parallel with this, at predetermined proper timings, the specimen and reagent sampling arms 13 and 22 are operated to work. First, for example, the specimen pipetting probe 13a is carried above the upper side of one of the specimen cup 10 . . . 10 which exists at a suction position at that time, and then lowered vertically into a specimen contained in the specimen cup 10. After this, the specimen pump control circuits 72 begins to operate. Hence, a pulsed driving voltage is applied through the drivers 73 to the specimen sampling pump 16. Therefore, the actuator 41 of the sampling pump 16 distorts and causes the specimen pipetting probe 13a to suck the specimen into it.

After this suction, the specimen sampling arm 13 is raised and rotated toward the sampling position above one of the reaction cells 30 . . . 30, and vertically lowered into the cell 30. Then the driving voltage to the actuator 41 is lowered down to zero or down to a certain value, or its polarity of the voltage pulse is reversed to the other side, so that the actuator 41 is released from its distortion so as to push out the sucked specimen into the reaction cell 30 positioned at the specimen sampling position at that time. In consequence, a desired volume of specimen should be discharged into the reaction cell 30. For other reaction cells 30 . . . 30, the same sampling will be done at their proper timings.

In the same manner as above, the reagent sampling arm 22 should be moved and the reagent sampling pump 25 should be operated. When a certain reaction cell 30 already charged with the specimen reaches the reagent sampling position, the reagent pipetting probe 22a will also come thereto and discharge a desired amount of a reagent into the reaction cell 30.

The reaction cell 30 already have been completed by the discharge of the specimen and reagent will then be turned on the disk 31. On its way, the specimen and reagent contained in the reaction cell 30 is mixed. While their turning (in a given period of turns, chemical reaction goes on), the reaction cells 30 . . . 30 in turn go through the optical measuring device 33, and changes in absorbance can be measured by it.

During the above-mentioned sampling, the piezoelectric sensors 45 and 45' in both the sampling pumps 16 and 25 detect the distortion (i.e., displacement) of their actuators 41 and 41'. The detected sensor outputs are sent to the specimen and reagent pump control circuits 72 and 74 along the feedback loops. Thus, in respose to the sensor outputs, the driving voltages to the pumps 16 and 25 are automatically regulated, if necessary, so as to comply with a specified desired value. As a result, the sampling quantity itself of each time is toward the desired volume by itself and more precise sampling will be given.

In parallel with the above feedback control, the operating quantities of the actuators 41 and 41' of the pumps 16 and 25 are calculated and the actual sampling quantities done by the pipetting probes 13a and 22a are calculated. In the data correction circuit 79, if necessary, the absorbances are corrected to be on the trace of absorbances corresponding to the specified sampling quantities, for example, on the proportional relation shown in FIG. 9. Consequently, even though there occured fluctuations to some extent among samplings, such correction can avoid decreases in accuracy of measured absorbances, and retain their high accuracy acheived by the above feedback control.

The absorbances thus-detected and -corrected are sent to the calculation circuit 81 in order to calculate desired measuring values such as the concentration of a substance being measured.

For instance, if the substance being measured is enzyme and the desired measuring value is its activity, the activity can be obtained by the following equation:

$$(IU)/1 = F \cdot {_\Delta}Abs \qquad (1)$$

$$F = 1/\epsilon \cdot (TV)/(SV) \cdot 1000 \qquad (2)$$

where (IU)/1: enzyme activity in specimen, $_\Delta$Abs : quantity of change in absorbance of reaction liquid, SV : sampling quantity, and TV : total quantity of reaction liquid (specimen plus reagent).

In case that a substance being measured is one of biochemical substances and the desired measuring value is its concentration [A], the concentration [A] can be obtained by the following equation:

$$[A] = \Delta E \cdot F \cdot [(SV)/(TV)] \qquad (3)$$

$$F = [(STD)/(\Delta E_{STD})] \cdot [(TV_{STD})/(SV_{STD})] \qquad (4)$$

where

[A] : concentration of substance in specimen (unknown), $\Delta E$ : absorbance in reaction liquid (or quantity of change in absorbance per unit time), (STD) : concentration of substance in standard liquid (known), $\Delta E_{STD}$ : absorbance of reaction liquid at a time of measuring standard liquid (or quantity of change in absorbance per unit time), $SV_{STD}$ : standard deviation at a time of measuring standard liquid, and $TV_{STD}$ : total quantity of reaction liquid (specimen plus reagent) at a time of measuring standard liquid.

In the foregoing equations (1) to (4), the specimen sampling qauntity (SV) and reagent sampling quantity are error factors for the measuring value. With those quantities, changed, the quantity (TV) of reaction liquid also changes, thereby influencing the measuring value.

In a conventional analyzer, the measurement accuracy of the entire analyzer was determined by the accuracy of the above error factors. In order, to secure high accuracy in sampling whose sampling volume is extremely small it was very important to have high measurement accuracy, thus having required sampling pumps of higher sampling accuracy.

However, in the present embodiment, even if sampling quantities of specimen and reagent, which are each sampled repeatedly, are slightly changed one after another, the sampling quantities exactly done are detected each time (refer to FIG. 5), and then the data of absorbance data are corrected, as shown in FIG. 9, if required. This means that the sampling pumps having extreme high sampling accuracy are not required. Finally measured results, such as concentration of substances, are certainly brought into higher accuracy nevertheless and the likelihood of measusrments are maintained high.

Because the sampling pumps themself are not required to have the highest accuracy in sampling, moderate accuracy and function in sampling are acceptable. Therefore, the sampling pumps should be simplified in construction, leading to compact size, and low cost in manufacturing.

Furthermore, in the above-mentioned sampling, when the tips of the specimen and reagent pipetting probes 13a and 22a have reached the liquid level (the level of the specimen and reagent), pressure changes are transmitted, through the tubes, to the actuators 41 and 41' (diaphragms), thus the actuators 41 and 41' displaces slightly toward a negative pressure side. This small displacement permits the piezoelectric sensors 45 and 45' to detect the arrival of the probes 13a and 22a at the liquid levels (refer to FIG. 6). This arrival is judged in the control circuits 72 and 74 in response to operating quantity signals calculated from the sensor outputs of the sensors 45 and 45'. Therefore, the control circuits 72 and 74 are able to control the start timings of sampling easily, without another liquid level sensors.

In parallel with the sampling operation, the error detection circuit 82 constantly examines the wave patterns of the operating quantities of the actuators 41 and 41', through the sensors 45 and 45' and the operating quantitiy calculation circuit 76. By comparing the detected patterns with that of the normal state shown in FIG. 7A, error states, such as air suction and Jamming with impurities, are properly found, and its results are displayed on the CRT 66 and printer. 67.

As apparent from above, the samping system, including the pipetting probe 13a (22a), the sampling pump 16 (25), and the calculation and detection circuits 76 and 82, includes a multipurpose sensing function: liquid level detectability and detection of error states. Therefore, it is not required to have a large number of independent sensors and processing circuits. As a result, their sensing construction is remarkably simplified and made compact, thus lowering manufacturing cost. In addition carry-over is reduced, which enhancing reliability of the analyzer.

For the present invention, further modifications are available. In the actuator 41 of the sampling pump 16 (25), it is possible to attach only one of the piezoelectric sheets 43 and 44 to one side of the metal plate 42. Also it is possible to use the actuator 41 in such a manner that one of the piezoelectric sheets 43 and 44 is for a pumping actuator body and the other for a sensor. Further, sampling specimen and reagent may be switched in order or done at the same time.

Second and third embodiments of the present invention will now be explained accoring to FIGS. 10 and 11.

Figures 10, 11:
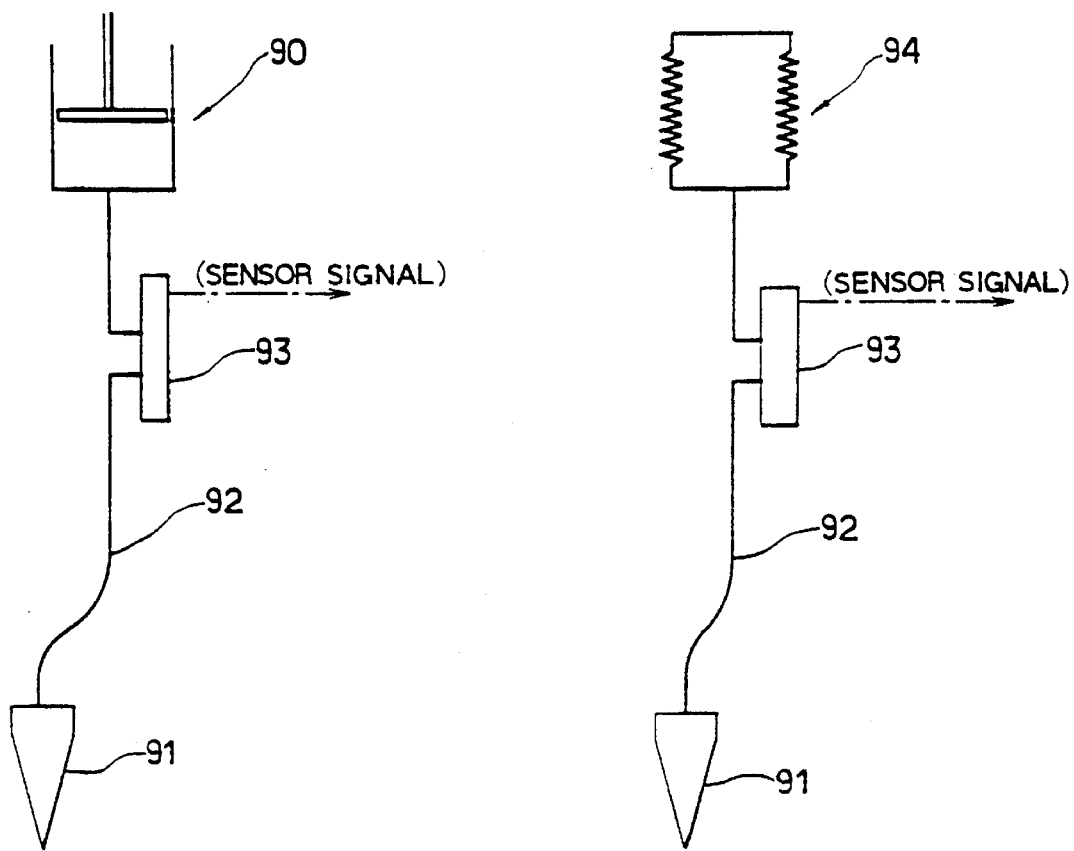
FIG. 10 is a block diagram showing a sampling system according to a second embodiment of the present invention.
FIG. 11 is a block diagram showing a sampling system according to a third embodiment of the present invention.

In FIG. 10 showing the second embodiment, a sampling system applying to an automatic chemical analyzer of the present invention is shown. There is provided a syringe-type pump 90 for sampling, instead of the aforementioned diaphragm type pump in which the piezoelectric type actuator is installed. The pumping chamber of the pump 90 is coupled with a pipetting probe 91 though a tube 92. In this case, independently of the pump 90, a sensor 93 is placed at a certain position of the tube 92 for detecting sampling quantities. This sensor 93 is composed in the same way as the piezoelectric-type sampling pump 16 (25) of the first embodiment, but works only for sensing sampling quantities.

A samping system, shown in FIG. 11 according to the third embodiment, is also applicable to an automatic chemical analyzer of the present invention. In this sampling system, a bellows-type pump 94 is provided, in addition to the pipetting probe 91, the tube 92, and the sensor 93 described in FIG. 10.

Figure 12:
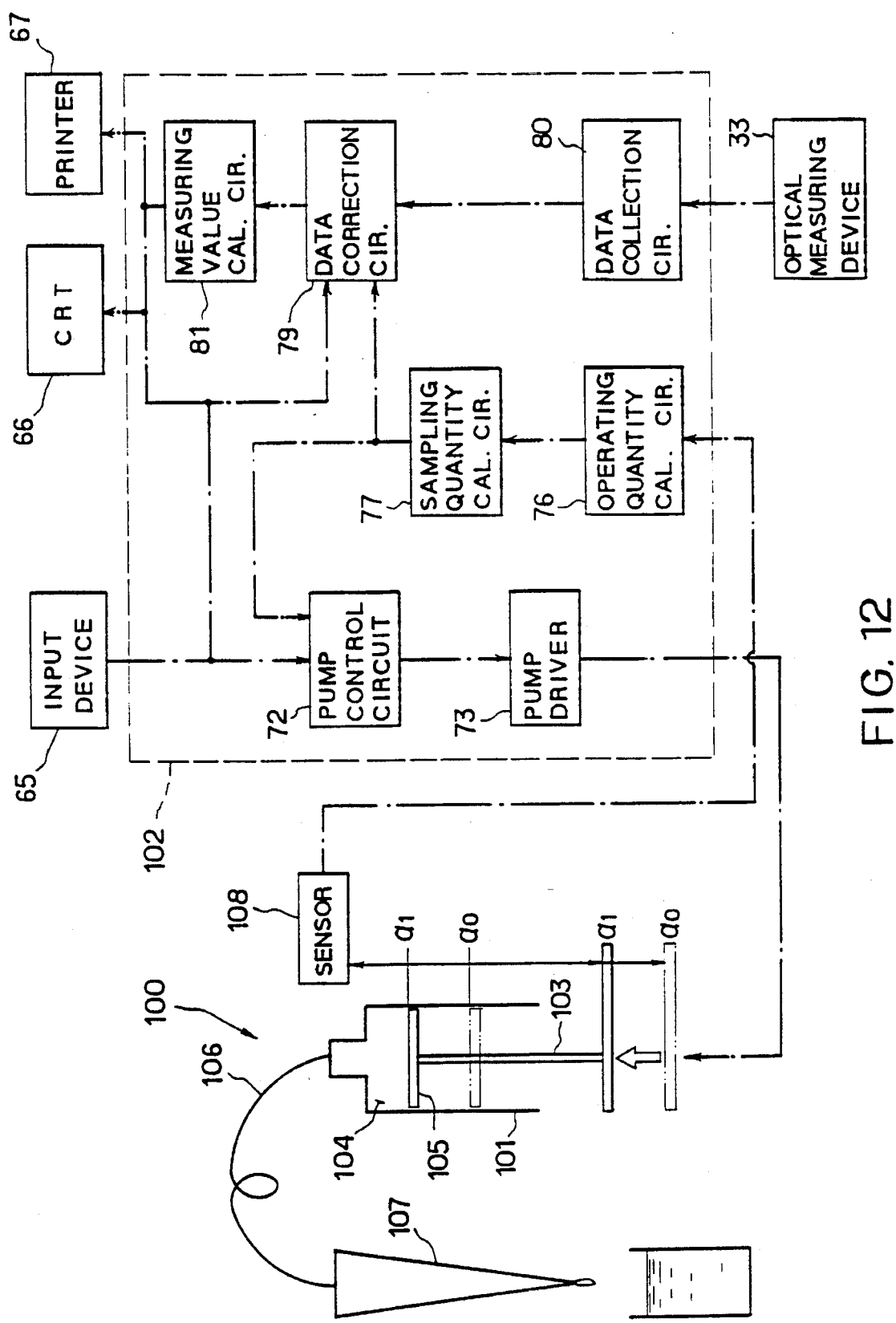
FIG. 12 is a block diagram showing a sampling system according to a fourth embodiment of the present invention.

Furthermore, a fourth embodiment of the present invention will now be explained according to FIG. 12. In this embodiment, the equivalent components to those of the first embodiment are given the same reference numbers.

A sampling system is shown in the figure, which is also applicable to the present invention. The sampling system comprises a reciprocating pump 100, as a sampling pump for specimen or reagent, having a syringe 101 therein, a control unit 102, an input device 65, a CRT 66, and a printer 67. When the reciprocating pump 100 operates by receiving a regulated driving voltage , a plunger 103 of the syringe 101 reciprocates in its axial direction. Pressure changes in a pumping chamber 104 separated by a piston 105 are transmitted, through a tube 106, to a pipetting probe 107 for specimen or reagent. As a result, it will be able to suck and discharge specimen or reagent through the pipetting probe 107, and sampling can be done.

Further, stroke quantities of the plunger 103 (i.e., a piston 105) are detected at its base by a laser displacement gauge 108 as a sensor, and detected sensor signals are supplied to the control unit 102.

The foregoing control unit 102 comprises a pump control circuit 72, a pump driver 73, an operating quantity calculation circuit 76, a sampling quantity calculation circuit 77, a data correction circuit 79, a data collecting circuit 80, and a measuring value calculation circuit 81, all of which has been described in the first embodiment and have the same function. If necessary, the combination of the pump control circuit and pump driver is arranged in parallel for sampling of specimen and reagent. Whereas the pump driver 73 will drive the pump 100, the sensor outputs from the gauge 108 will be sent to the operating quantity calculation circuit 76, in which the oparating quantities of the pump 100 are calculated.

In the sampling quantity calculation circuit 77, changes in the oparating quantities thus-calculated are examined, and the stroke distance "a0–a1" is determined. And using a known inner diameter r of the syringe 101, a sampling quantity of one time, "$\pi r^2 \cdot (a0-a1)$", is obtained.

The data of the sampling quantities thus-calculated are used to properly correct absorbance data by the same manner as the first embodiment. On the basis of the corrected absorbance data, desired measuring values, such as concentration, are precisely calculated.

As a result, as mentioned earlier, even though mechanical precision of each component is moderate, finally measured values are sufficiently high in accuracy and reliability. This leads to low cost in manufacturing the analyzer.

In the fourth embodiment, different modifications of a sensing mechanism are possible. Scanning a laser beam or arranging parallel light beams can be adopted, thus being able to measure the stroke distance "a0–a1" of the plunger 103. Further, a direct detection of sampling quantities can be also done. A pulse driving source including a piezoelectric element therein is used for discharge sampling liquid in the form of droplets of a small quantity. A laser beam is arranged to integrate the number of the droplets, and on the basis of the integrated value and known factors including the diameter of droplets, the volumes of the droplets are again integrated to estimate a sampling quantity.

Furthermore, a microcomputer may be installed in the above-said control unit and may have a program equivalent in function to the circuits which have been described.

The present invention can also be applied to a sampling system having a plurality of pipetting probes for each of the specimen sampling and reagent sampling.

What we claim is:

1. An automatic chemical analyzer having a sampling system by which a liquid selectively including a specimen and a reagent is sampled by sucking the liquid at one position on the automatic chemical analyzer and discharging the sucked liquid at another position on the automatic chemical analyzer, resultant chemical reaction between the specimen and the reagent being detected as light absorbance data and collected for chemical analysis of the specimen, said sampling system comprising:

a pump having a pumping chamber for sucking and discharging the liquid;

a tube having one end connected to the pumping chamber;

a nozzle connected to another end of the tube;

means for driving the pump to sample a certain quantity of the liquid by sucking and discharging the liquid;

a sensor for sensing an operating quantity of the pump and generating a signal corresponding to the operating quantity;

means for determining the sampling quantity sampled by the pump in response to the signal from the sensor; and means for correcting the collected light absorbance fluctuations in data in accordance with the determined sample quantity even with fluctuations in the certain quantity sampled.

2. The automatic chemical analyzer according to claim 1, wherein said sampling system consists of two independent sampling systems and each of the sampling systems is provided for each of the specimen and reagent, respectively.

3. The automatic chemical analyzer according to claim 2, wherein said pump is a reciprocating pump having a syringe therein.

4. The automatic chemical analyzer according to claim 3, wherein said sensor has a sensing element sensing a mechanical motion of the syringe.

5. The automatic chemical analyzer according to claim 4, wherein said sensing element is a laser displacement gauge.

6. The automatic chemical analyzer according to claim 2, wherein said sensor is placed at a given position in the tube.

7. The automatic chemical analyzer according to claim 6, wherein said sensor includes a piezoelectric element for sensing the operating quantity.

8. The automatic chemical analyzer according to claim 2, wherein said pump is a bellows type pump.

9. The automatic chemical analyzer according to claim 1, wherein said pump has a container in which an inner space of a certain volume is formed and an actuator is arranged in the inner space to form the pumping chamber therein, the actuator comprising a base plate having two opposing sides thereon and a piezoelectric element attached to the base plate.

10. The automatic chemical analyzer according to claim 9, wherein said piezoelectric element is composed of a single piezoelectric plate attached to either one of the two opposing sides of the base plate.

11. The automatic chemical analyzer according to claim 9, wherein said piezoelectric element is composed of two piezoelectric plates each of which is attached to a separate one of the two opposing sides of the base plate.

12. The automatic chemical analyzer according to claim 11, wherein the driving means includes an electric circuit for controlling the driving voltage in a manner that, for sucking the liquid, the piezoelectric element displaces from an original state to a distortion state to increase the volume of the pumping chamber and, for discharging the liquid, the piezoelectric element returns from the distortion state toward the original state.

13. The automatic chemical analyzer according to claim 12, wherein said sensor is a piezoelectric sensor for sensing distortion of the actuator and for generating a signal corresponding to the distortion, the piezoelectric sensor being attached to the base plate.

14. The automatic chemical analyzer according to claim 13, wherein one of said two piezoelectric plates is partly cut out to form a cutout portion and the piezoelectric sensor is attached to the cutout portion.

15. The automatic chemical analyzer according to claim 13, wherein said driving means includes a means for controlling the driving voltage on the basis of the sampling quantity determined.

16. The automatic chemical analyzer according to claim 13, further comprising means for detecting a level of the liquid sucked through the nozzle in response to the signal supplied from the piezoelectric sensor.

17. The automatic chemical analyzer according to claim 13, further comprising means for detecting an error state in sampling on the basis of the signal supplied from the piezoelectric sensor.

18. The automatic chemical analyzer according to claim 17, wherein said error state is a state of air suction from the nozzle.

19. The automatic chemical analyzer according to claim 17, wherein said error state is a state of jamming into the nozzle with impurities contained in the liquid.

20. The automatic chemical analyzer according to claim 17, further comprising means for displaying the error state detected.

21. The automatic chemical analyzer according to claim 9, further comprising means for calculating a value of a desired measuring object using the absorbance data corrected by the correcting means.

22. The automatic chemical analyzer according to claim 21, wherein said desired measuring object is a concentration of a biochemical substance contained in the specimen.

23. The automatic chemical analyzer according to claim 21, wherein said desired measuring object is an activity of a substance contained in the specimen.

24. The automatic chemical analyzer according to claim 17, wherein said error state detecting means includes means for comparing a wave pattern of the signal supplied from the piezoelectric sensor with a predetermined normal-state wave pattern of the signal supplied from the piezoelectric sensor in order to detect the error state.

* * * * *